(12) United States Patent
Schek et al.

(10) Patent No.: US 8,968,725 B2
(45) Date of Patent: Mar. 3, 2015

(54) GENIPIN CROSS-LINKED FIBRIN GELS

(75) Inventors: Rachel Schek, Milton, VT (US); Arthur J. Michalek, Burlington, VT (US); James C. Iatridis, New York, NY (US)

(73) Assignee: University of Vermont and State Agricultural College, Burlington, VT (US)

( * ) Notice: Subject to any disclaimer, the term of this patent is extended or adjusted under 35 U.S.C. 154(b) by 0 days.

(21) Appl. No.: 13/309,906

(22) Filed: Dec. 2, 2011

(65) Prior Publication Data

US 2012/0189584 A1 Jul. 26, 2012

Related U.S. Application Data

(60) Provisional application No. 61/419,177, filed on Dec. 2, 2010.

(51) Int. Cl.
| | | |
|---|---|---|
| A61P 17/02 | (2006.01) | |
| A61P 19/04 | (2006.01) | |
| A61K 47/42 | (2006.01) | |
| A61K 35/32 | (2006.01) | |
| C07K 14/745 | (2006.01) | |
| A61P 41/00 | (2006.01) | |
| A61K 9/00 | (2006.01) | |

(52) U.S. Cl.
CPC .............. *C07K 14/745* (2013.01); *A61K 9/0014* (2013.01); *A61K 47/42* (2013.01)
USPC ........................... 424/93.7; 530/384; 514/773

(58) Field of Classification Search
USPC ............................ 424/93.7; 530/382; 514/773
See application file for complete search history.

(56) References Cited

U.S. PATENT DOCUMENTS

| | | | | |
|---|---|---|---|---|
| 2004/0124564 | A1* | 7/2004 | Noorjahan et al. | 264/488 |
| 2005/0125077 | A1* | 6/2005 | Harmon et al. | 623/23.72 |
| 2005/0209699 | A1* | 9/2005 | Slivka et al. | 623/17.16 |

OTHER PUBLICATIONS

Schek et al., Genipin-crosslinked fibrin hydrogels as a potential adhesive to augment intervertebral disc annulus repair, Eur Cell Mater, 2011; 21: 373-383.*
Dare et al., Mar. 13, 2009; Genipin Cross-Linked Fibrin Hydrogels for in vitro Human Articular Cartilage Tissue-Engineered Regeneration, Cells Tissues Organs, DOI: 10.1159/000209230.*
Linnes et al., 2007; A fibrinogen-bases precision microporous scaffold for tissue engineering, Biomaterials, 28: 5298-5306.*
Iatridis et al., 1999; Shear Mechanical Properties of Human Lumbar Annulus Fibrosus, Journal of Orthopaedic Research, 17: 732-737.*
NIH, NIH 3T3 Cell Line, Accessed Nov. 26, 2012, online at: nih3t3.com/.*
Linnes et al., A fibrinogen-based precision microporous scaffold for tissue engineering, Biomaterials, 28 (2007) pp. 5298-5306.*
Ahmed, T.A., et al. (2008) "Fibrin: A Versatile Scaffold for Tissue Engineering Applications" Tissue Eng Part B Rev.
Balestrini, J.L., (2006) "Equibiaxial Cyclic Stretch Stimulates Fibroblasts to Rapidly Remodel Fibrin." J Biomech 39:2983-2990.
Bedran-Russo, A.K., et al. (2007) "Application of Crosslinkers to Dentin Collagen Enhances the Ultimate Tensile Strength." J Biomed Mater Res B Appl Biomater 80:268-272.
Chen, Y.S., et al. (2005) "An in Vivo Evaluation of a Biodegradable Genipin-Cross-Linked Gelatin Peripheral Nerve Guide Conduit Material." Biomaterials 26:3911-3918.
Chong, A.K., et al. (2007) "Bone Marrow-Derived Mesenchymal Stem Cells Influence Early Tendon-Healing in a Rabbit Achilles Tendon Model." J Bone Joint Surg Am 89:74-81.
Connelly, J.T., et al. (2004) "The Influence of Cyclic Tension Amplitude on Chondrocyte Matrix Synthesis: Experimental and Finite Element Analyses." Biorheology 41:377-387.
Eyrich, D., et al. (2007) "Long-Term Stable Fibrin Gels for Cartilage Engineering." Biomaterials 28:55-65.
Hecker, L., et al. (2005) "Development of a Three-Dimensional Physiological Model of the Internal Anal Sphincter Bioengineered in Vitro from Isolated Smooth Muscle Cells" Am J Physiol Gastrointest Liver Physiol 289:G188-196.
Hojo, M., et al. (2003) "Induction of Vascular Endothelial Growth Factor by Fibrin as a Dermal Substrate for Cultured Skin Substitute" Plast Reconstr Surg 111:1638-1645.
Huang, L. L, et al. (1998) "Biocompatibility Study of a Biological Tissue Fixed with a Naturally Occurring Crosslinking Reagent" J Biomed Mater Res 42:568-576.
Huang, Y.C., et al. (2005) "Rapid Formation of Functional Muscle in Vitro Using Fibrin Gels" J Appl Physiol 98:706-713.
Johnson, T.S., et al. (2004) "Integrative Repair of Cartilage with Articular and Nonarticular Chondrocytes" Tissue Eng 10:1308-1315.
Mi, F.L., et al. (2002) "In Vivo Biocompatibility and Degradability of a Novel Injectable-Chitosan-Based Implant" Biomaterials 23:181-191.
Mwale, F., et al. (2005) "Biological Evaluation of Chitosan Salts Cross-Linked to Genipin as a Cell Scaffold for Disk Tissue Engineering" Tissue Eng 11:130-140.
Nieponice, A., et al. (2007) "Mechanical Stimulation Induces Morphological and Phenotypic Changes in Bone Marrow-Derived Progenitor Cells within a Three-Dimensional Fibrin Matrix" J Biomed Mater Res A 81:523-530.
Passaretti, D., et al. (2001) "Cultured Chondrocytes Produce Injectable Tissue-Engineered Cartilage in Gel Polymer" Tissue Eng 7:805-815.

(Continued)

*Primary Examiner* — Karen Cochrane Carlson
*Assistant Examiner* — Jennifer M. H. Tichy
(74) *Attorney, Agent, or Firm* — Nixon Peabody LLP

(57) ABSTRACT

The invention provides a genipin cross-linked fibrin gel. The ratio of genipin to fibrin in the gel ranges from about 0.1:1 to about 10:1 (genipin:fibrin). The gel can be hydrogel. Also provided is method for repairing tissue defects by administering the gel to site of tissue defect.

18 Claims, 10 Drawing Sheets

(56) References Cited

OTHER PUBLICATIONS

Peretti, G.M., et al. (2006) "Review of Injectable Cartilage Engineering Using Fibrin Gel in Mice and Swine Models" Tissue Eng 12:1151-1168.

Rowe, S. L., et al. (2007) "Influence of Thrombin Concentration on the Mechanical and Morphological Properties of Cell-Seeded Fibrin Gels" Acta Biomater 3:59-67.

Sell, S.A., et al. (2008) "Cross-Linking Methods of Electrospun Fibrinogen Scaffolds for Tissue Engineering Applications" Biomed Mater 3:45001.

Sung, H. W., et al. (2003) "Crosslinking of Biological Tissues Using Genipin and/or Carbodiimide" J Biomed Mater Res A 64:427-438.

Tsai, C. C., et al., (2000) In Vitro Evaluation of the Genotoxicity of a Naturally Occurring Crosslinking Agent (Genipin) for Biologic Tissue Fixation. J Biomed Mater Res 52:58-65.

* cited by examiner

GENIPIN CROSS-LINKED FIBRIN GELS

RELATED APPLICATIONS

This application claims benefit under 35 U.S.C. §119(e) of the U.S. Provisional Application No. 61/419,177, filed Dec. 2, 2010, content of which is incorporated herein by reference in its entirety.

GOVERNMENT SUPPORT

This invention was made with government support under grant no. R01 AR051146 awarded by the National Institutes of Health. The government has certain rights in the invention.

FIELD OF THE INVENTION

The invention relates to methods and compositions for repair of intervertebral disc annulus defects.

BACKGROUND OF THE INVENTION

Degeneration of intervertebral discs (IVD) is associated with low back pain and is a serious public health problem in the US, affecting more that 25% of adults (Deyo et al., 2006). Current therapies for treatment of pain resulting from IVD degeneration include spinal fusion, discectomy, and total disc replacement. Each of these techniques, however, has limitations. Fusion and rigid fixation limits mobility and may lead to degeneration of discs in the adjacent motion segments, while discectomy results in loss of disc height and alters the biomechanics of the spine (Lee, 1988; Schlegel et al., 1996). These methods, on the whole, do not repair the degenerated disc or restore its original function. As a result, there has been recent increasing interest in preserving as much of the disc tissue as possible and in developing new techniques to truly repair damaged discs. Specifically, strategies to replace and regenerate the nucleus pulposus (NP), the central, gelatinous region of the IVD, have been the subject of much work (Di Martino et al., 2005; Hegewald et al., 2008; Sebastine and Williams, 2007). The limited success that has been achieved by these methods, however, stems in part from the fact that the annulus fibrosus (AF), the outer ring of the IVD, is not repaired. The AF is necessarily damaged during surgery to remove or repair the NP, and yet a functional, intact AF is key to preventing re-herniation of the NP and retention of any NP replacement device (Alini et al., 2002; Wilke et al., 2006). Thus, the ultimate success of such a treatment depends in part on the restoration of AF function.

Methods for repairing damaged AF are currently limited largely to sutures and modified sutures, which do not compensate for the loss of AF tissue or restore the lost biomechanical properties (Bron et al., 2009a). An appealing alternative is the development of a tissue engineering scaffold to repair the gap in the AF and contain the NP or its replacement. Such a scaffold would need to meet the following three requirements: match the mechanical properties of the AF tissue, support the growth of disc cells, and adhere to the surrounding tissues under physiological levels of strain. A number of materials have been investigated for this purpose including gels, bioglass, collagen, silk and degradable polymers such as polycaprolactone and polyglycolic acid. (Chang et al., 2007; Helen and Gough, 2008; Mizuno et al., 2004; Nerurkar et al., 2007; Sato et al., 2003; Shao and Hunter, 2007; Wan et al., 2008). While many of these materials show promise, none have satisfactorily addressed the need for fixing the scaffold within the annular defects. To ensure a scaffold remains in place and encourage the formation of new tissue, it is critical that any material be able to strongly adhere and be fully integrated with the native annulus tissue.

SUMMARY OF THE INVENTION

The present disclosure provides genipin cross-linked fibrin gels. In some embodiments, gels have physical or mechanical properties that are suitable for their use in repair of intervertebral disc annulus defects. The ratio of genipin to fibrin in the gel can range from 0.1:1 to 10:1.

In another aspect, provided herein is a method of repairing a defect in a intervertebral disc annulus in a subject in need thereof, the method comprising placing a genipin cross-linked fibrin gel at an intervertebral disc annulus defect site in a subject.

DETAILED DESCRIPTION OF THE INVENTION

Figure 1A:
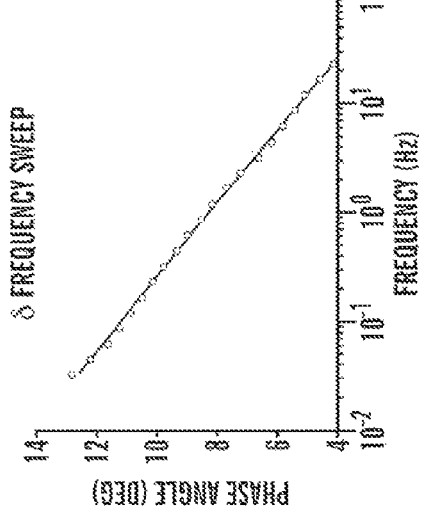
FIGS. 1A-1D show representative model fits (-) to experimental data (o o) for |G*| frequency sweep (FIG. 1A), |G*| strain sweep (FIG. 1B), δ frequency sweep (FIG. 1C), and δ strain sweep (FIG. 1D). Black arrows indicate slippage between the specimen and the rheometer platens. Measurements after this point were not analyzed.
Figure 1B:
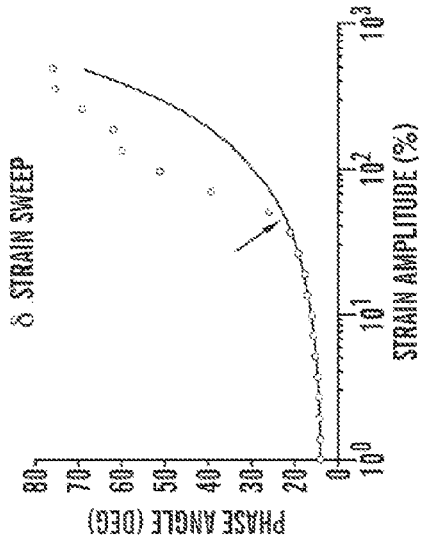
Figure 1C:
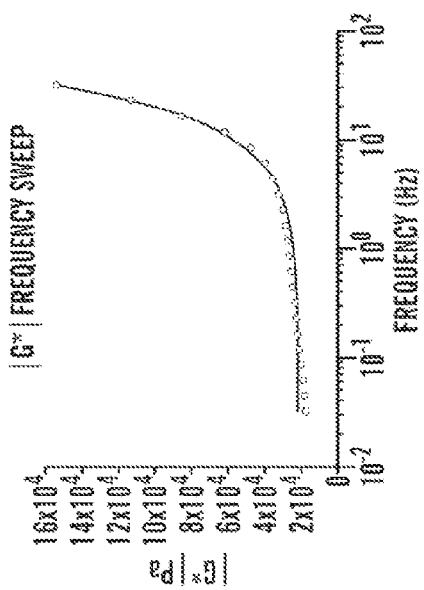
Figure 1D:
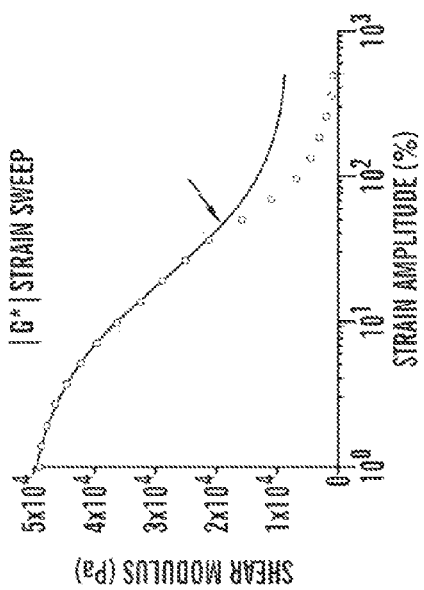

In one aspect, provided herein is fibrin gel which is cross-linked with genipin. In some embodiments, the genipin cross-linked fibrin gel has chemical, physical or mechanical properties that are suitable for their use in repair of intervertebral disc annulus defects.

In some embodiments, the gel is a hydrogel. As used herein, the term "hydrogel" refers to a three-dimensional polymeric structure that itself is insoluble in water but which is capable of absorbing and retaining large quantities of water to form a stable, often soft and pliable, structure.

Without limitations, the gel can comprise any ratio of genipin to fibrin. Accordingly, the gel can comprise a genipin to fibrin ratio in the range from about 0.1:1 to about 10:1. In some embodiments of the aspects described herein, the gel comprises a genipin:fibrin ratio from 0.1:1 to 5:1, from 0.1:1 to 4:1, from 0.1:1 to 2:1, from 0.1:1 to 1.5:1, from 0.1:1 to 1:1, from 0.1:1 to 0.9:1, from 0.2 to 0.8:1, and/or from 0.25 to 0.75:1. In some embodiments, the gel comprises a genipin:fibrin ratio of 0.20:1 to 0.5:1. In some embodiments, the gel comprises a genipin:fibrin ratio of 0.25:1 or 0.5:1.

The inventors have discovered that that the gels can be made from fibrin solutions comprising a wide concentration range of fibrin. Accordingly, the gel can be made from a fibrin solution comprising from about 50 mg/ml to about 500 mg/ml, from about 100 mg/ml to about 400 mg/ml, 150 mg/ml to about 300 mg/ml, 20 mg/ml to about 250 mg/ml of fibrin. In some embodiments of the aspects described herein, the gel is made from a fibrin solution comprising about 200 mg/ml of fibrin. In some embodiments of the aspects described herein, the gel is made from a fibrin solution comprising about 250 mg/ml of fibrin. In still some other embodiments of the aspects described herein, the gel is made from a fibrin solution comprising about 300 mg/ml of fibrin.

Genipin (Methyl (1R,2R,6S)-2-hydroxy-9-(hydroxymethyl)-3-oxabicyclo[4.3.0]nona-4,8-diene-5-carboxylate) is an aglycone derived from an iridoid glycoside called geniposide present in fruit of Gardenia jasminoides. It has a low acute toxicity, with $LD_{50}$ i.v. 382 mg/kg in mice; therefore, much less toxic than glutaraldehyde and many other commonly used synthetic cross-linking regents. It is also used for pharmaceutical purposes, such as choleretic action for liver diseases control. Genipin is a known naturally occurring crosslinking agent. It has been shown that genipin can dimerize in the presence of nucleophiles such as primary amines and that the C7-C8 double bond and the C10 primary alcohol of genipin are necessary for the crosslinking process. Genipin can be prepared by oxidation followed by reduction and hydrolysis or by enzymatic hydrolysis of the parent compound geniposide. Alternatively, racemic genipin can be prepared synthetically.

As used herein, the term "genipin" includes genipin, its derivatives, analogs and any stereoisomers or mixtures of stereoisomers of genipin. Thus, while genipin is described herein, it is to be understood genipin, its derivatives, analogs, any stereoisomers, or mixtures of stereoisomers of genipin, or any combination thereof, can be used as the cross-linker. Exemplary genipin analogues and derivatives include, but are not limited to, those described in U.S. Pat. No. 6,162,826; No. 6,262,083; and No. 7,649,014 content of all of which is incorporated herein by reference.

Generally, the term "fibrin" refers to polymers of fibrin, formed by polymerization following cleavage of fibrinogen by thrombin. However, as used herein, "fibrin" does not only refer to the product of fibrinogen produced by action of thrombin during the clotting or coagulation of blood but further includes any mixture of fibrin and fibrinogen which may occur during formation of fibrin from fibrinogen using thrombin and, thus, includes any ratio of fibrinogen/fibrin. Additionally, fibrin refers to any type of fibrin or fibrinogen. Fibrin, therefore, includes monomeric and dimeric fibrinogen molecules having the mono-mer structure (AαBβγ), as well as molecules having the monomer structure (Aα$_\epsilon$Bβγ), and other hybrid molecules, whether naturally occurring, modified, or synthetic. The term "fibrin" refers generally to human fibrinogen and fibrin, but can include fibrinogen and fibrin of any species, especially mammalian species.

For applications in repair of tissue defect, the gels need to have modulus similar to the native tissue. Accordingly, in some embodiments, the gel has an elastic modulus in the range between $10^{-2}$ and $10^3$ kPa. As used herein, the term "elastic modulus" refers to an object or substance's tendency to be deformed elastically (i.e., non-permanently) when a force is applied to it. Generally, the elastic modulus of an object is defined as the slope of its stress-strain curve in the elastic deformation region. Specifying how stress and strain are to be measured, including directions, allows for many types of elastic moduli to be defined. Young's modulus (E) describes tensile elasticity, or the tendency of an object to deform along an axis when opposing forces are applied along that axis; it is defined as the ratio of tensile stress to tensile strain. It is often referred to simply as the elastic modulus. The bulk modulus (K) describes volumetric elasticity, or the tendency of an object to deform in all directions when uniformly loaded in all directions; it is defined as volumetric stress over volumetric strain, and is the inverse of compressibility. The bulk modulus is an extension of Young's modulus to three dimensions. Three other elastic moduli are Poisson's ratio, Lamé's first parameter, and P-wave modulus.

In some embodiments of the aspects described herein, the gel has a shear modulus from about 50 kPa to about 110 kPa. As used herein, the term "shear modulus" refers to the ratio of a measured shear stress to shear strain that is used to produce that stress. The shear modulus or modulus of rigidity (G or μ) describes an object's tendency to shear (the deformation of shape at constant volume) when acted upon by opposing forces. The shear modulus is part of the derivation of viscosity. Generally, the shear modulus can be determined by ASTM test method E143-87 (1998).

In some embodiments, the gel has a dynamic modulus of from about 50 kPa to about 110 kPa. As used herein, the term "dynamic modulus" refers to the ratio of stress to strain under vibratory conditions. Dynamic modulus can be calculated from data obtained from either free or forced vibration tests, in shear, compression, or elongation.

In some embodiments, the modulus is measured at 10% strain at 1 Hz.

In some embodiments of the aspects described herein, the gel comprises a bioactive agent. As used herein, "bioactive agents" or "bioactive materials" refer to naturally occurring biological materials, for example, extracellular matrix materials such as fibronectin, vitronection, and laminin; cytokines; growth factors and differentiation factors; and cells. "Bioactive agents" also refer to artificially synthesized materials, molecules or compounds that have a biological effect on a biological cell, tissue or organ.

Suitable growth factors and cytokines include, but are not limited, to stem cell factor (SCF), granulocyte-colony stimulating factor (G-CSF), granulocyte-macrophage stimulating factor (GM-CSF), stromal cell-derived factor-1, steel factor, VEGF, TGFβ, platelet derived growth factor (PDGF), angiopoeitins (Ang), epidermal growth factor (EGF), bFGF, HNF, NGF, bone morphogenic protein (BMP), fibroblast growth factor (FGF), hepatocye growth factor, insulin-like growth factor (IGF-1), interleukin (IL)-3, IL-1α, IL-1β, IL-6, IL-7, IL-8, IL-11, and IL-13, colony-stimulating factors, thrombopoietin, erythropoietin, flt3-ligand, and tumor necrosis factor α (TNFα). Other examples are described in Dijke et al., "Growth Factors for Wound Healing", Bio/Technology, 7:793-798 (1989); Mulder G D, Haberer P A, Jeter K F, eds. Clinicians' Pocket Guide to Chronic Wound Repair. 4th ed. Springhouse, Pa.: Springhouse Corporation; 1998:85; Ziegler T. R., Pierce, G. F., and Herndon, D. N., 1997, International Symposium on Growth Factors and Wound Healing: Basic Science & Potential Clinical Applications (Boston, 1995, Serono Symposia USA), Publisher: Springer Verlag.

In some embodiments, suitable bioactive agents include, but are not limited to, therapeutic agents, i.e. pharmaceutically active agents. As used herein, the term "therapeutic agent" refers to a substance used in the diagnosis, treatment, or prevention of a disease. Any therapeutic agent known to those of ordinary skill in the art to be of benefit in the diagnosis, treatment or prevention of a disease is contemplated as a therapeutic agent in the context of the present invention. Therapeutic agents include pharmaceutically active compounds, hormones, growth factors, enzymes, DNA, plasmid DNA, RNA, siRNA, viruses, proteins, lipids, pro-inflammatory molecules, antibodies, antibiotics, anti-inflammatory agents, anti-sense nucleotides and transforming nucleic acids or combinations thereof. Any of the therapeutic agents may be combined to the extent such combination is biologically compatible.

Exemplary pharmaceutically active compounds (e.g., therapeutic agents) include, but are not limited to, those found in *Harrison's Principles of Internal Medicine*, $13^{th}$ Edition, Eds. T. R. Harrison et al. McGraw-Hill N.Y., N.Y.; Physicians Desk Reference, $50^{th}$ Edition, 1997, Oradell N.J., Medical Economics Co.; Pharmacological Basis of Therapeutics, $8^{th}$ Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete content of all of which are herein incorporated in its entirety.

In some embodiments, bioactive agent is a wound healing agent or a wound care agent. As used herein, the term "wound healing agent," refers to a bioactive agent that actively promotes wound-healing processes over days, weeks, or months. Agents that promote wound-healing include, but are not limited to, anti-inflammatory agents, growth factors, agents which inhibit free radical formation, and bacteriostatic or bacteriocidal agents.

Anti-inflammatory agents are agents that inhibit or prevent an immune response in vivo. Exemplary anti-inflammatory agents include: (i) agents which inhibit leukocyte migration into the area of injury ("leukocyte migration preventing agents"), and antihistamines. Representative leukocyte migration preventing agents include silver sulfadiazine, acetylsalicylic acid, indomethacin, and Nafazatrom. Representative anti-histamines include pyrilamine, chlorpheniramine, tetrahydrozoline, antazoline, and other anti-inflammatories such as cortisone, hydrocortisone, beta-methasone, dexamethasone, fluocortolone, prednisolone, triamcinolone, indomethacin, sulindac, its salts and its corresponding sulfide, and the like.

Exemplary agents which inhibit free radical formation include, but are not limited to, antioxidants that inhibit the formation and/or action of oxide products, superoxide dismutase (SOD), catalase, glutathione peroxidase, b-carotene, ascorbic acid, transferrin, ferritin, ceruloplasmin, and desferoxamine a-tocophenol.

Representative bacteriostatic or bacteriocidal agents include antibacterial substances such as (3-lactam antibiotics, such as cefoxitin, n-formamidoyl thienamycin and other thienamycin derivatives, tetracyclines, chloramphenicol, neomycin, gramicidin, bacitracin, sulfonamides; aminoglycoside antibiotics such as gentamycin, kanamycin, amikacin, sisomicin and tobramycin; nalidixic acids and analogs such as norfloxican and the antimicrobial combination of fluoroalanine/pentizidone; nitrofurazones, and the like.

Additional exemplary wound-healing agents include, for example, aminoxyls, furoxans, nitrosothiols, nitrates and anthocyanins; nucleosides, such as adenosine; and nucleotides, such as adenosine diphosphate (ADP) and adenosine triphosphate (ATP); neurotransmitter/neuromodulators, such as acetylcholine and 5-hydroxytryptamine (serotonin/5-HT); histamine and catecholamines, such as adrenalin and noradrenalin; lipid molecules, such as sphingosine-1-phosphate and lysophosphatidic acid; amino acids, such as arginine and lysine; peptides such as the bradykinins, substance P and calcium gene-related peptide (CGRP), and proteins, such as insulin, vascular endothelial growth factor (VEGF), and thrombin.

In some embodiments, the gel comprises a cell, e.g. a biological cell. Cells useful for incorporation into the gel can come from any source, for example human, rat or mouse. Cells amenable to be incorporated into the composition include, but are not limited to, stem cells (embryonic stem cells, mesenchymal stem cells, bone-marrow derived stem cells and hematopoietic stem cells), chrondrocytes progenitor cells, pancreatic progenitor cells, myoblasts, fibroblasts, keratinocytes, neuronal cells, glial cells, astrocytes, pre-adipocytes, adipocytes, vascular endothelial cells, hair follicular stem cells, endothelial progenitor cells, mesenchymal cells, neural stem cells and smooth muscle progenitor cells. In some embodiments, the cell is a disc cell.

In some embodiments, the cell is a genetically modified cell. A cell can be genetically modified to express and secrete a desired compound, e.g. a bioactive agent, a growth factor, differentiation factor, cytokines, and the like. Methods of genetically modifying cells for expressing and secreting compounds of interest are known in the art and easily adaptable by one of skill in the art.

Differentiated cells that have been reprogrammed into stem cells can also be used. For example, human skin cells reprogrammed into embryonic stem cells by the transduction of Oct3/4, Sox2, c-Myc and Klf4 (Junying Yu, et. al., *Science*, 2007, 318, 1917-1920 and Takahashi K. et. al., *Cell*, 2007, 131, 1-12).

In some embodiments, the gel comprises a therapeutically effective amount of the bioactive agent. The phrase "therapeutically-effective amount" as used herein means that amount of a compound, material, or composition comprising a compound of the present invention which is effective for producing some desired therapeutic effect in at least a subpopulation of cells in an animal at a reasonable benefit/risk ratio applicable to any medical treatment. In other words, a therapeutically effective amount means that amount necessary to delay the onset of, inhibit the progression of, or halt altogether the particular condition being treated. Determination of a therapeutically effective amount is well within the capability of those skilled in the art. Generally, a therapeutically effective amount can vary with the subject's history, age, condition, sex, as well as the severity and type of the medical condition in the subject, and administration of other agents.

The bioactive agent can be covalently linked to the gel through a linker. The linker can be a cleavable linker or non-cleavable linker, depending on the application. As used herein, a "cleavable linker" refers to linkers that are capable of cleavage under various conditions. Conditions suitable for cleavage can include, but are not limited to, pH, UV irradiation, enzymatic activity, temperature, hydrolysis, elimination and substitution reactions, redox reactions, and thermodynamic properties of the linkage. In many cases, the intended nature of the conjugation or coupling interaction, or the desired biological effect, will determine the choice of linker group.

In some embodiments, the gel is functionalized with a binding molecule that binds with a bioactive molecule. These binding molecules are also referred to as affinity molecules herein. The binding molecule can be bound covalently (directly or through a linker) or non-covalently to the matrix. The binding molecule can be selected such that it can bind to any part of bioactive molecule that is accessible.

As used herein, the term "binding molecule" or "affinity molecule" refers to any molecule that is capable of binding a bioactive molecule. Representative examples of affinity molecules include, but are not limited to, antibodies, antigens, lectins, proteins, peptides, nucleic acids (DNA, RNA, PNA and nucleic acids that are mixtures thereof or that include nucleotide derivatives or analogs); receptor molecules, such as the insulin receptor; ligands for receptors (e.g., insulin for the insulin receptor); and biological, chemical or other molecules that have affinity for another molecule, such as biotin and avidin. The binding molecules need not comprise an entire naturally occurring molecule but may consist of only a portion, fragment or subunit of a naturally or non-naturally occurring molecule, as for example the Fab fragment of an antibody.

Nucleic acid based binding molecules include aptamers. As used herein, the term "aptamer" means a single-stranded, partially single-stranded, partially double-stranded or double-stranded nucleotide sequence capable of specifically recognizing a selected non-oligonucleotide molecule or group of molecules. In some embodiments, the aptamer recognizes the non-oligonucleotide molecule or group of molecules by a mechanism other than Watson-Crick base pairing or triplex formation. Aptamers can include, without limitation, defined sequence segments and sequences comprising nucleotides, ribonucleotides, deoxyribonucleotides, nucleotide analogs, modified nucleotides and nucleotides comprising backbone modifications, branchpoints and nonnucleotide residues, groups or bridges. Methods for selecting aptamers for binding to a molecule are widely known in the art and easily accessible to one of ordinary skill in the art.

In some embodiments of the aspects described herein, the binding molecules are polyclonal and/or monoclonal antibodies and antigen-binding derivatives or fragments thereof. Well-known antigen binding fragments include, for example, single domain antibodies (dAbs; which consist essentially of single VL or VH antibody domains), Fv fragment, including single chain Fv fragment (scFv), Fab fragment, and F(ab')2 fragment. Methods for the construction of such antibody molecules are well known in the art. Accordingly, as used herein, the term "antibody" refers to an intact immunoglobulin or to a monoclonal or polyclonal antigen-binding fragment with the Fc (crystallizable fragment) region or FcRn binding fragment of the Fc region. Antigen-binding fragments may be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies and polypeptides that contain at least a portion of an immunoglobulin that is sufficient to confer specific antigen binding to the polypeptide. The terms Fab, Fc, pFc', F(ab') 2 and Fv are employed with standard immunological meanings (Klein, Immunology (John Wiley, New York, N.Y., 1982); Clark, W. R. (1986) The Experimental Foundations of Modern Immunology (Wiley & Sons, Inc., New York); and Roitt, I. (1991) Essential Immunology, 7th Ed., (Blackwell Scientific Publications, Oxford)). Antibodies or antigen-binding fragments specific for various antigens are available commercially from vendors such as R&D Systems, BD Biosciences, e-Biosciences and Miltenyi, or can be raised against these cell-surface markers by methods known to those skilled in the art.

In some embodiments, the binding molecule binds with a cell. Without wishing to be bound by a theory, a molecule that binds with a cell can do so by binding with a cell-surface marker or a cell-surface molecule. These binding molecules that bind with a cell are also referred to as cell binding molecules. In some further embodiments, the binding molecule binds with a cell-surface marker but does not cause initiation of downstream signaling event mediated by that cell-surface marker. Binding molecules specific for cell-surface molecules include, but are not limited to, antibodies or fragments thereof, natural or recombinant ligands, small molecules, nucleic acids and analogues thereof, intrabodies, aptamers, lectins, and other proteins or peptides.

As used herein, a "cell-surface marker" refers to any molecule that is present on the outer surface of a cell. Some molecules that are normally not found on the cell-surface can be engineered by recombinant techniques to be expressed on the surface of a cell. Many naturally occurring cell-surface markers present on mammalian cells are termed "CD" or "cluster of differentiation" molecules. Cell-surface markers often provide antigenic determinants to which antibodies can bind to.

Accordingly, as defined herein, a "binding molecule specific for a cell-surface marker" refers to any molecule that can selectively react with or bind to that cell-surface marker, but has little or no detectable reactivity to another cell-surface marker or antigen. Without wishing to be bound by theory, affinity molecules specific for cell-surface markers generally recognize unique structural features of the markers. In some embodiments of the aspects described herein, the affinity molecules specific for cell-surface markers are polyclonal and/or monoclonal antibodies and antigen-binding derivatives or fragments thereof.

In some embodiments, the cell binding molecule is a ligand that binds to a receptor on the surface of a cell. Such a ligand can be a naturally occurring molecule, a fragment thereof or a synthetic molecule or fragment thereof. In some embodiments, the ligand is non-natural molecule selected for binding with a target cell. High throughput methods for selecting non-natural cell binding ligands are known in the art and easily available to one of skill in the art. See for example, Anderson, et al., Biomaterial microarrays: rapid, microscale screening of polymer-cell interaction. *Biomaterials* (2005) 26:4892-4897; Anderson, et al., Nanoliter-scale synthesis of arrayed biomaterials and application to human embryonic stem cells. *Nature Biotechnology* (2004) 22:863-866; Orner, et al., Arrays for the combinatorial exploration of cell adhesion. *Journal of the American Chemical Society* (2004) 126: 10808-10809; Falsey, et al., Peptide and small molecule microarray for high throughput cell adhesion and functional assays. *Bioconjugate Chemistry* (2001) 12:346-353; Liu, et al., *Biomacromolecules* (2001) 2(2): 362-368; and Taurniare, et al., *Chem. Comm.* (2006): 2118-2120.

Gels described herein can additionally include one or more additives. Additives may be resolving (biodegradable) polymers, mannitol, starch sugar, inosite, sorbitol, glucose, lactose, saccharose, sodium chloride, calcium chloride, amino acids, magnesium chloride, citric acid, acetic acid, hydroxyl-butanedioic acid, phosphoric acid, glucuronic acid, gluconic acid, poly-sorbitol, sodium acetate, sodium citrate, sodium phosphate, zinc stearate, aluminium stearate, magnesium stearate, sodium carbonate, sodium bicarbonate, sodium hydroxide, polyvinylpyrolidones, polyethylene glycols, carboxymethyl celluloses, methyl celluloses, starch, micro-particles, nano-particles, aprotinin, Factor XIII, or their mixtures. Without wishing to be bound by a theory, one or more additives in the gel can alter (e.g. reduce or increase) the rate of gel degradation.

A gel described herein can be combined with another material, e.g. a biomaterial, to form a composite material. The term "biomaterial" as used herein refers in general to biocompatible naturally occurring materials. Exemplary biomaterials include, but are not limited to, biopolymers, sponges, silk, decellularized tissues, and gelatin. The term "biopolymer" as used herein refers to either a naturally occurring polymer, or a synthetic polymer that is compatible with a biological system or that mimics naturally occurring polymers. Exemplary biopolymers include, but are not limited to, oligosaccharides, polysaccharides such as glycosaminoglycans, peptides, proteins, oligonucleotides, nucleic acids, polyketides, peptoids, hydrogels, poly(glycols) such as poly(ethylene glycol), collage, silk, and polylactates.

The gels described herein can be used in tissue engineering and repair. For example, a gel described herein can be used to repair defects in cartilage, muscle, skin, tendon/ligament. In another example, an implant can be coated with a gel before implanting. In yet another example, a degradable material can be coated the gel to allow the degradable material to adhere to a tissue of interest. This can allow repairing of larger defect sizes by providing a support material that is coated with the gel thus allowing coverage of the larger defect size.

In another aspect, provided herein is a method of repairing a tissue defect in a subject in need thereof, the method comprising administering to the subject a gel described herein. As used herein, the term "tissue defect" refers to any medical abnormality of a tissue, including, but not limited to, a damaged tissue, a deficient tissue, a degraded tissue, a traumatised tissue. In fact, any abnormality of a tissue that can be repaired by a method of the invention is included in the term "tissue defect".

Tissue defects, include, but are not limited to, wounds, ulcers, burns, natural defects, such as birth defects, and any other defects of bodily tissue, including skin, bone, cartilage, muscle, tendon., ligament, gastrointestinal organs, and other internal organs. The term "wound" refers to damage to any tissue in a living organism. A wound can be in a soft tissue, such as the spleen, or in a hard tissue, such as bone. A wound can have been caused by any agent, including traumatic injury, disease, infection, surgical intervention, or natural causes.

In some embodiments, the tissue defect is an intervertebral disc annulus defect.

As used herein, the term "repair" refers to any correction, reinforcement, reconditioning, remedy, making up for, making sound, renewal, mending, patching, or the like that restores function. Accordingly, the term "repair" can also mean to correct, to reinforce, to recondition, to remedy, to make up for, to make sound, to renew, to mend, to patch or to otherwise restore function. In some embodiments "repair" includes full repair and partial repair of an intervertebral disc annulus defect. Furthermore, the term "repair" also includes treatment, prevention or amelioration of at least one symptom associated with or caused by an intervertebral disc annulus defect. By "treatment," "prevention," or "amelioration" is meant delaying or preventing the onset, reversing, alleviating, ameliorating, inhibiting, slowing down or stopping the progression, aggravation or deterioration the progression or severity of a condition associated with an intervertebral disc annulus defect. In one embodiment, the symptoms of an intervertebral disc annulus defect are alleviated by at least 5%, at least 10%, at least 20%, at least 30%, at least 40%, or at least 50%.

As used herein, the term "administering" means placing the gel at the site of the tissue defect, i.e. local administration. Without limitations this can be accomplished by injecting the gel into the defect. Alternatively, or in addition, the gel can be placed in the defect location by a surgical procedure. In some embodiments, the gel is delivered as liquid to the defect site.

In some embodiments, a solution comprising the components of the gel, e.g. genipin, fibrin (or fibrinogen) and any other components can be placed at the defect site and the crosslinking initiated by the appropriate trigger, such as by addition of thrombin.

As used herein, a "subject" means a human or animal. Examples of subjects include primates (e.g., humans, and monkeys).Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. The terms, "patient" and "subject" are used interchangeably herein. A subject can be male or female.

Preferably, the subject is a mammal. The mammal can be a human, non-human primate, mouse, rat, dog, cat, horse, or cow, but are not limited to these examples. Mammals other than humans can be advantageously used as subjects that represent animal models of human disease or disorders. In addition, the methods and compositions described herein can be used to treat domesticated animals and/or pets.

A subject can be one who has been previously diagnosed with or identified as in need of repair for a tissue defect. A subject can be one who is currently being treated for a tissue defect.

In some embodiments of the aspects described herein, the method further comprising diagnosing a subject for a tissue defect. The methods of diagnosing intervertebral disc annulus defects are well known in the art.

In some embodiments, the method further comprising selecting a subject diagnosed with a tissue defect before onset of administration of the genipin cross-linked gel.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments of the aspects described herein, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean ±1%.

The singular terms "a," "an," and "the" include plural referents unless context clearly indicates otherwise. Similarly, the word "or" is intended to include "and" unless the context clearly indicates otherwise. Thus for example, references to "the method" includes one or more methods, and/or steps of the type described herein and/or which will become apparent to those persons skilled in the art upon reading this disclosure and so forth.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

As used herein, the term "transgene" refers to a nucleic acid which codes for a specific protein or RNA product and which is capable of becoming integrated into at least one chromosome of an organism. The transgene nucleic acids includes the promoter region from the same gene or another gene. The transgene nucleic acid can be obtained from another species or the same species as the host organism.

To the extent not already indicated, it will be understood by those of ordinary skill in the art that any one of the various embodiments herein described and illustrated may be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Materials and Methods
Gel Fabrication:

Fibrinogen isolated from bovine plasma (Sigma) was dissolved in phosphate buffered saline at concentrations of 50, 100, 150, 200, 250, or 300 mg/ml. Thrombin isolated from bovine plasma (Sigma) was dissolved in phosphate buffered saline (PBS) at a concentration of 100 U/ml. Genipin (Wako, Richmond, Va.) was dissolved in dimethyl sulfoxide (Fisher Scientific) at a concentration of 400 mg/ml. The fibrinogen was pipetted into molds as specified below; thrombin and genipin were mixed together and then added to the fibrinogen in quantities specified below. Genipin quantities were determined such that desired genipin:fibrin weight ratios could be obtained (i.e., to create a 0.25:1 gel for cell culture testing, 600 µl of 200 mg/ml fibrinogen was mixed with 75 µl of genipin). The gels were allowed to rest for 24 hours to completely crosslink prior to mechanical testing or cell seeding. Pilot studies (not shown) demonstrated that genipin:fibrin concentration of 1:1 and 2:1 resulted in nearly zero cell survival. Therefore, we have tested ratios of 0.25:1, 0.5:1, and 0:1 as a control. The ratio of 0:1 was fibrin gel alone.

Rheological Testing:

Samples for rheometer testing were creating using a custom made Teflon molds with cylindrical wells 5 mm in diameter and 5 mm deep. Into each well, 50 µl of the fibrinogen was pipetted, followed by 5 µl of thrombin mixed with sufficient genipin to create the desired ratio of genipin:fibrin. The resulting gel specimens were approximately 2.5 mm thick.

Gel dynamic stiffness tests were carried out using a rheometer (TA Instruments) equipped with flat platens covered with 100 grit sand paper (Gator Grit) and a humidified chamber. The test protocol was adapted from Bron et al. (Bron et al., 2009b) and consisted of a 20 minute equilibration at 0.1N of axial compression followed by a dynamic frequency sweep at 10% strain from 0.032 to 32 Hz. The protocol concluded with a strain sweep at 0.5 Hz from 1 to 500% strain. Dynamic modulus magnitude, $|G^*|$, and phase angle, $\delta$, were calculated at each point of the frequency and strain sweeps. Parameters from both sweeps demonstrated power law dependence on frequency and strain, and were thus characterized by fitting the following functions using a least squares routine in Matlab (Mathworks Inc.) (FIG. 1).

$$|G^*|(\omega) = a + b\omega^{\alpha_{|G^*|}}, \delta(\omega) = c + d\omega^{\alpha_\delta}$$

$$|G^*|(\gamma) = j + k(\gamma+\Gamma)^{\beta_{|G^*|}}, \delta(\gamma) = m + n\gamma^{\beta_\delta}$$

Five parameters from the model fit were used to compare $|G^*|$ and $\delta$ across groups, and with human AF tissue. For the frequency sweep, dynamic modulus was characterized by its value at 1 Hz, $|G^*|_{1\,Hz}$ which is equivalent to parameters a+b, and its dependence on frequency was characterized by power law exponent, $\alpha_{|G^*|}$. Phase angle was likewise characterized its value at 1 Hz, $\delta_{1\,Hz}$ which is equivalent to parameters c+d, and its power law exponent, $\alpha_\delta$. For the strain sweep, accurate description of the experimental data also required a strain offset term. Therefore, dynamic modulus during the strain sweep was characterized by strain offset, $\Gamma$, modulus at the offset strain, $|G^*|_{\Gamma0}$, and strain dependence exponent $\beta_{|G^*|}$. Phase angle during the strain offset was accurately described with 2 parameters, its value at 1% strain, $\delta_{1\%} = m+n$, and strain dependence exponent for $\delta$, $\beta_\delta g$. The dependence of these nine parameters on fibrin and genipin concentrations was assessed using a two way ANOVA with factors fibrin concentration (200, 250 & 300 mg/ml), and relative genipin concentration (i.e., as given by genipin:fibrin ratio of 0:1, 0.25:1 & 0.5:1).

In order to assess the suitability of the genipin cross-linked fibrin gels for tissue repair, the rheological testing protocol was also performed on thirteen human AF specimens with an average age of 53±16. Average Thompson grade of these discs was 3, indicating a tissue with mild to moderate degeneneration. Model fit parameters were compared between the gel groups and the native tissue using unpaired t-tests with the significant p value adjusted to <0.005 to account for multiple comparisons.

Figure 2:
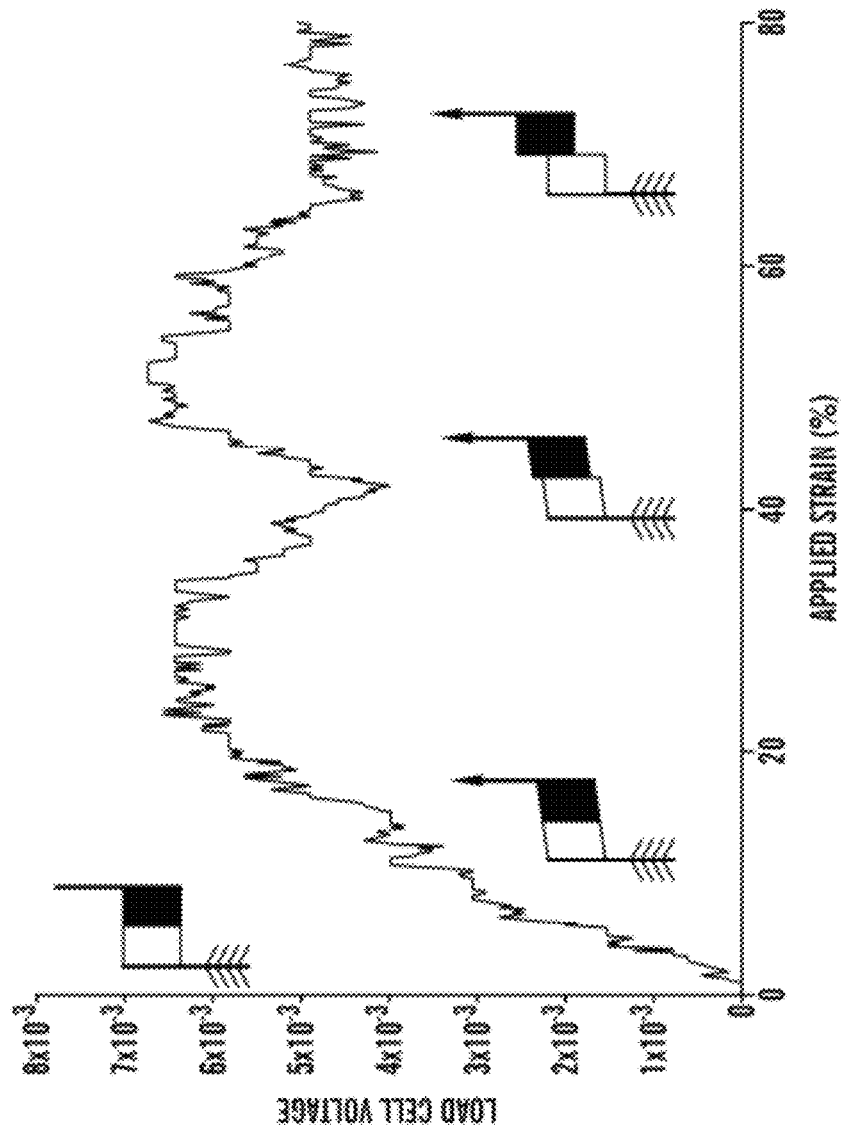
FIG. 2 is a representative plot of load cell voltage vs. applied strain for a bi-layered lap test. Schematics show bi-layered specimen initially (a), under shear (b), at initial failure (c), and completely failed (d).
Figure 3A:
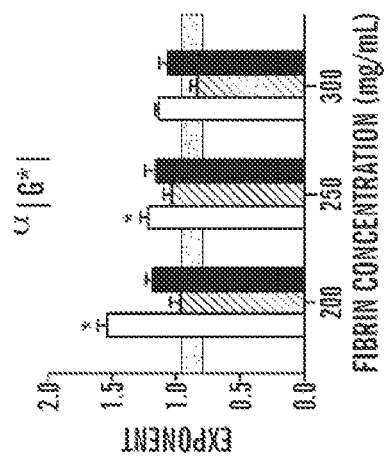
FIGS. 3A-3D show 3b shows the average frequency sweep model fit parameters shear modulus ±SEM for gels with varying fibrin concentrations and genipin:fibrin ratios. * indicates significantly different from human AF ($p<0.005$).
Figure 3C:
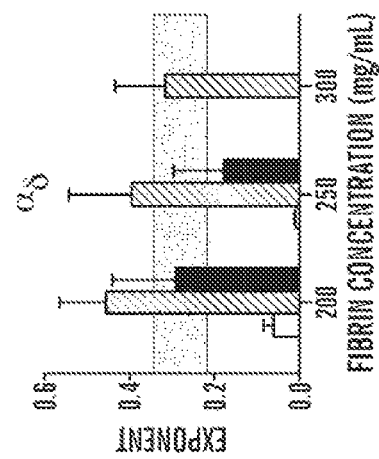
Figure 3B:
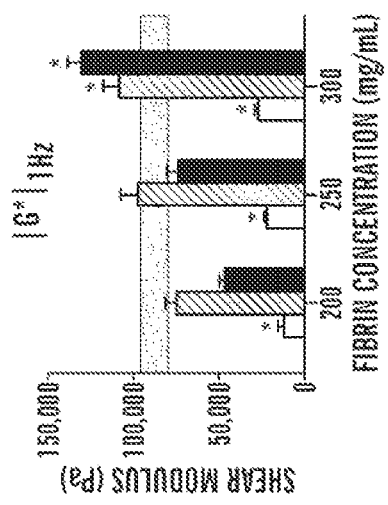
Figure 3D:
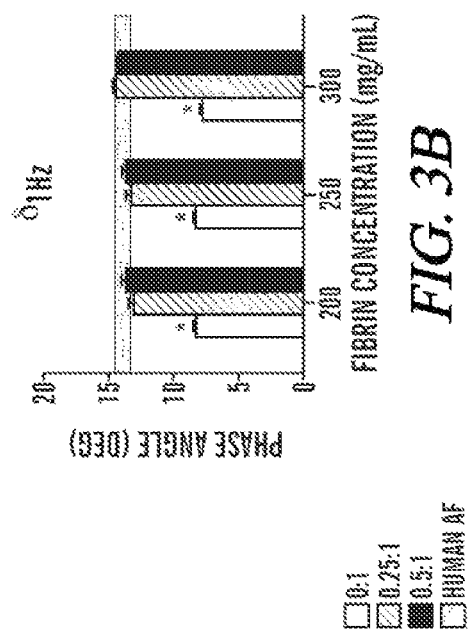
Figure 4A:
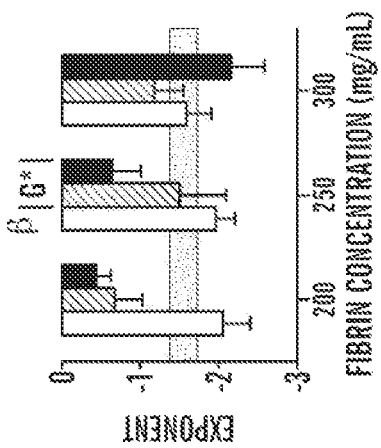
FIGS. 4A-4E show shows the average strain sweep model fit parameters ±SEM for gels with varying fibrin concentrations and genipin:fibrin ratios. * indicates not significantly different from human AF ($p<0.005$).
Figure 4B:
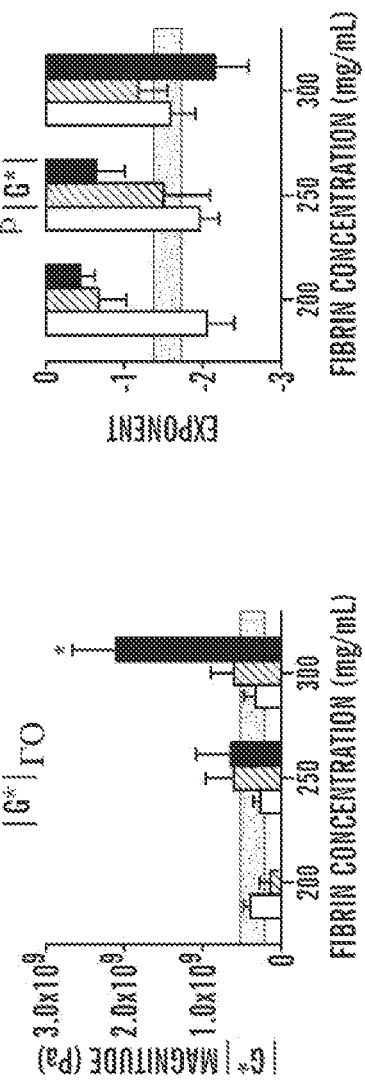
Figure 4C:
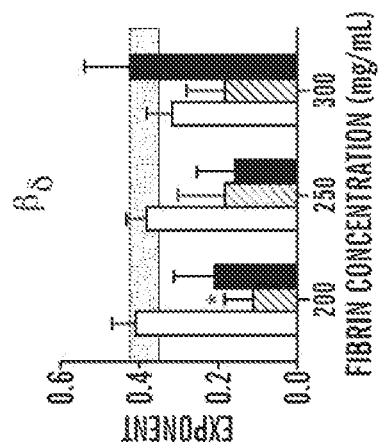
Figure 4D:
Figure 4E:
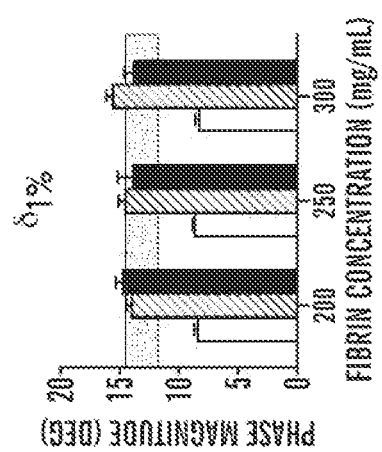

Lap Testing:

Gel-tissue adhesion was characterized by a modified lap test carried out using a custom built axial testing machine using a linear actuator (www.physikinstrumente.com). The upper and lower faces of the bi-layered specimen were adhered to brass platens using cyanoacrylate glue (Loctite 410 Gel). In order to differentiate between adhesion and static boundary friction, platen spacing was adjusted to minimize axial force on the specimen. One platen was then displaced in order to shear the specimen at a constant rate of 1%/s to 100%. Pilot studies showed that this magnitude was sufficient to ensure specimen failure. Specimen failure strain was assessed by identifying peak stress on the resulting load versus strain plot (FIG. 2). Mode of failure was determined visually for each specimen and recorded.

Cell Culture:

Human AF cells were obtained from tissue removed by a surgeon performing discectomy procedures with IRB approval and patient consent; discs were obtained from patients with an average age of 45±14 and graded as either moderate or severely degenerate. Discectomy tissues were first rinsed in a wash solution of 1.5% fungizone (Gibco) and 3% penicillin-streptomycin (Gibco) in phosphate buffered saline (Gibco) and then digested in 50 ml of Dulbecco's Modified Eagle Medium (DMEM, Gibco) containing 0.2% pronase (Sigma), 1% penicillin-streptomycin, and 0.5% fungizone for one hour at 37° C. After one hour, 0.2% collagenase (Sigma) was added to the digest solution and the digest was continued for an additional 4 hours. The digest was then filtered through a 70 μm nylon filter, centrifuged, and cells resuspended and plated into flasks. Cells were fed every 3-4 days with DMEM supplemented with 10% fetal bovine serum (Gibco), 1% penicillin-streptomycin, 0.5% fungizone, and 50 μg/ml ascorbic acid (Sigma). Cells used for viability experiments were P3-P4.

Gels were created in the wells of 6-well tissue culture plates. Into each well, 600 μl of 200, 250, or 300 mg/ml fibrinogen was pipetted. Thrombin (60 μl/well) and genipin were added to obtain genipin: fibrin of 0:1, 0.25:1, or 0.5:1 (n=3). After 24 hours, the gels were rinsed with PBS and 30,000 human disc cells were plated in each well. Cells were fed with supplemented DMEM every two days and allowed to grow on the gels for 1, 3, or 7 days and then rinsed with PBS. To assess the number of live cells adhered on the surface of the gels, they were incubated with a solution of 4 mM calcein in PBS (Invitrogen) for 30 minutes at 37° C. Cells were then imaged on an Olympus upright BX microscope equipped with a Chroma GFP filter cube and a Leica R3 camera. Photographs were processed using ImageJ; they were thresholded and the total number of cells was counted. From each experimental well, five fields of view were captured and counted. For each gel formulation at each time point, a total of 15 values were averaged and standard error calculated.

Results

Gel Fabrication:

Gels formed readily in both the Teflon molds and cell culture dishes. Gels set in less than 5 minutes and evidence of crosslinking (appearance of dark blue color) was apparent within 2 hours. Following the 24 hour curing, cross-linked gels were very firm to the touch and easily removable from the Teflon mold. Gels fabricated without genipin were more difficult to remove from the mold and more easily torn during handling.

Stiffness Results from Rheological Testing:

Rheological testing indicated that material properties of this genipin cross-linked fibrin gel follow power law relationships (c.o.d=0.84±0.28) with strain amplitude and frequency, the parameters of which are tuneable by varying fibrin concentration and genipin:fibrin concentration. The two way ANOVA showed that nearly all parameters were significantly affected by fibrin concentration, genipin:fibrin ratio, and their interaction (p-values are summarized in Table 1, and parameter values are in FIGS. 3 and 4), although some exceptions were found particularly for the strain sensitivity of several material parameters.

TABLE 1

Two way anova showing effects of fibrin and relative genipin concentrations on frequency and strain dependent mechanical properties.

| | Frequency Modulus | | Phase Angle | | | Strain Modulus | | Phase Angle | |
| --- | --- | --- | --- | --- | --- | --- | --- | --- | --- |
| | $G^*|_{1\,Hz}$ | $\alpha_{|G^*|}$ | $\delta_{1\,Hz}$ | $\alpha_\delta$ | $\Gamma$ | $|G^*|_{\Gamma 0}$ | $\beta_{|G^*|}$ | $\delta_{1\%}$ | $\beta_\delta$ |
| Fibrin | <0.001 | <0.001 | 0.080 | <0.001 | 0.015 | 0.709462 | <0.001 | 0.436 | 0.050 |
| Relative Genipin | <0.001 | <0.001 | 0.008 | <0.001 | 0.567 | 0.467944 | <0.001 | 0.045 | <0.001 |
| Interaction | 0.074 | <0.001 | 0.541 | 0.018 | 0.995 | 0.546036 | <0.001 | 0.352 | 0.088 |

Gels made with 250 mg/ml of fibrin and either 0.25:1 or 0.5:1 genipin:fibrin appear to be the most suitable for mimicking the shear behavior of native tissue, as these samples were not significantly different from human AF in any of the nine calculated parameters. The frequency sweep showed that genipin cross-linked fibrin gels generally demonstrate greater strain rate stiffening (increase in |G*| with increasing frequency) than the native tissue, with significance achieved either without genipin or with 0.5:1 genipin:fibrin at lower fibrin concentrations. Strain rate viscosity effects (change in δ with increasing frequency) were not significantly different from native in any of the gel groups. The strain dependency exponents, $\beta_{|G^*|}$ and $\beta_\delta$, were not significantly different from native AF for most gel groups. Both magnitude parameters, as calculated by both the frequency and strain sweeps, were significantly lower in the gels without genipin at all fibrin concentrations.

Adhesion Results from Lap Testing:

The modified lap test resulted in an average failure strain±SD of 26±7%. The mode of failure was equally distributed between slippage of the gel-tissue interface and fracture of the gel itself.

Figure 5B:
FIGS. 5A and 5B are images of calcein stained cells after 3 days grown on 200 mg/ml fibrin gel containing no genipin (FIG. 5A) or with a genipin:fibrin ratio of 0.25:1 (FIG. 5B).
Figure 5A:
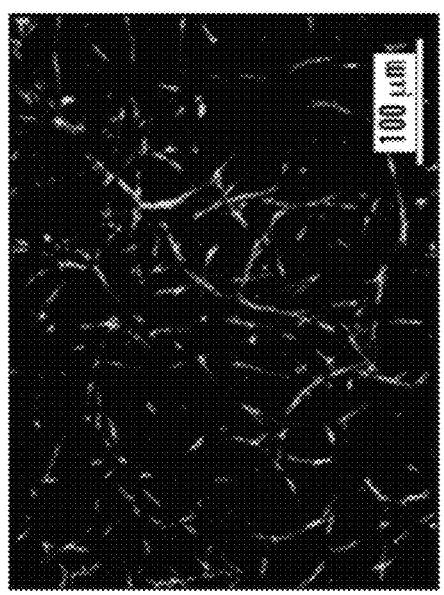

Cell Viability:

Disc cells assumed a spindle morphology that is typical when grown on tissue culture plastic, when grown on fibrin gel alone (i.e., ratio of 0:1) (FIG. 5). When grown on the genipin containing gels, the disc cells maintained a round shape and did not exhibit cell processes extending across the surface of the gel. This difference was observed for all fibrinogen concentrations and genipin:fibrin ratios; the presence of genipin at these levels was sufficient to alter the morphology.

Figure 6A:
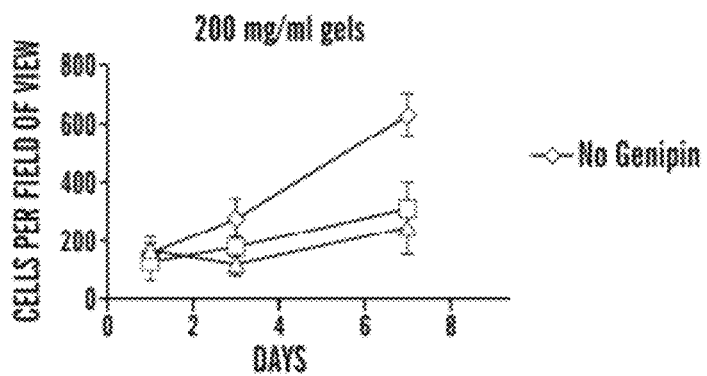
FIGS. 6A-6C show the multiplication of cells over time on the cross-linked fibrin gels prepared from 200 mg/ml (FIG. 6A), 250 mg/ml (FIG. 6B) and 300 mg/ml (FIG. 6C) fibrin solution. Cell number is per field of view.
Figure 6B:
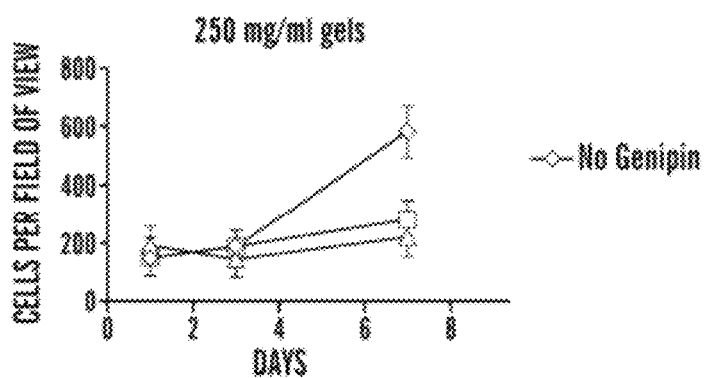
Figure 6C:
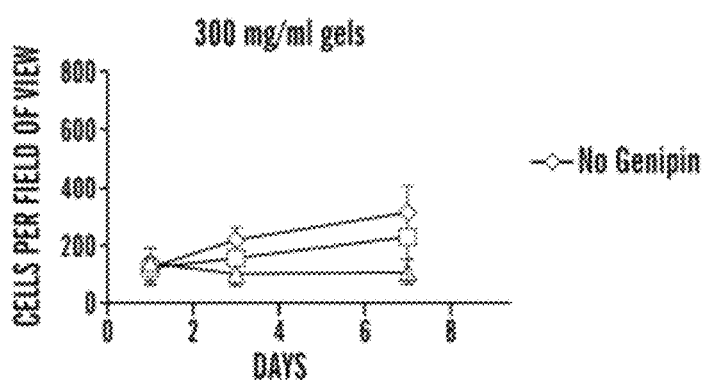
Figure 7:
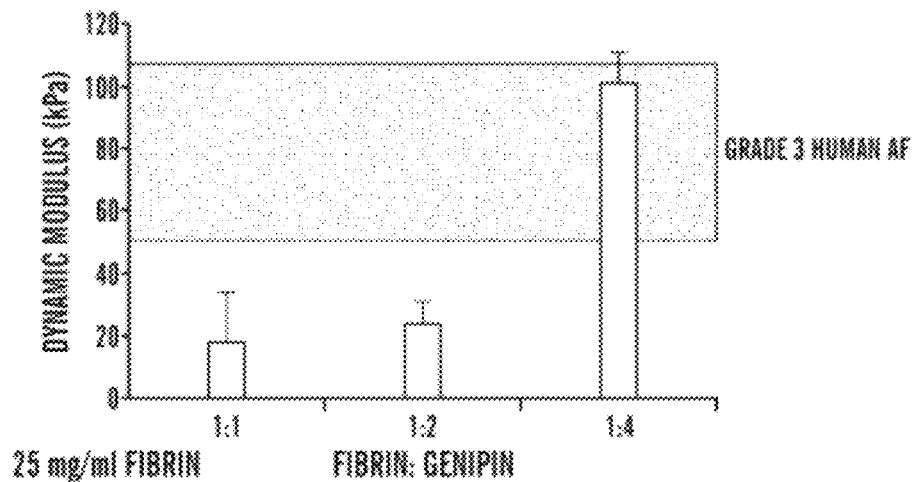
FIG. 7 shows the dynamic modulus of gels prepared from a 25 mg/ml fibrin solution with different fibrin:genipin ratios.
Figure 8:
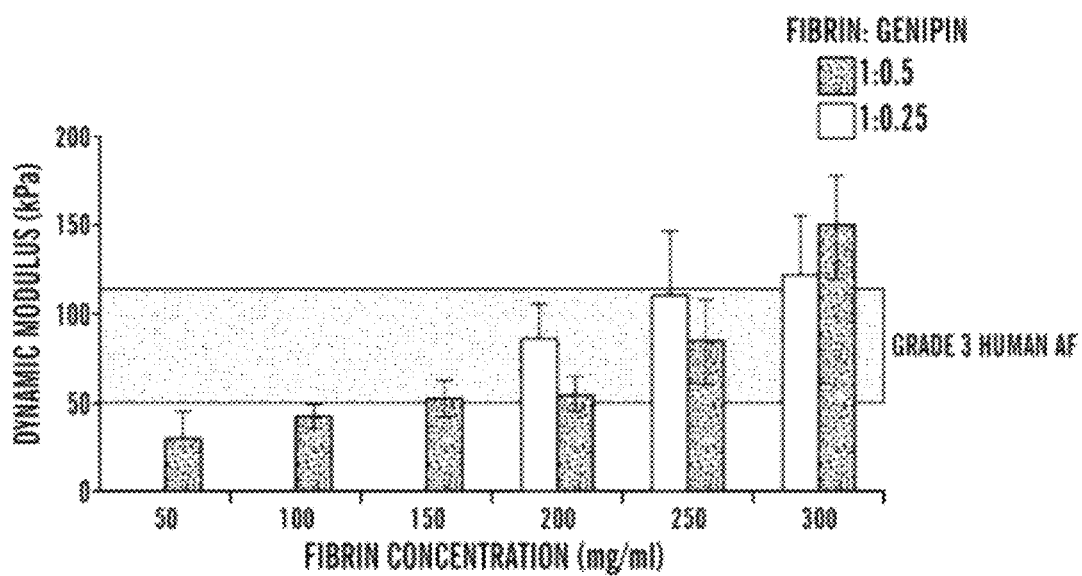
FIG. 8 shows the dynamic modulus of a gel prepared from different fibrin concentration solutions with fibrin:genipin ratio of 1:0.25 or 1:0.5.
Figure 9:
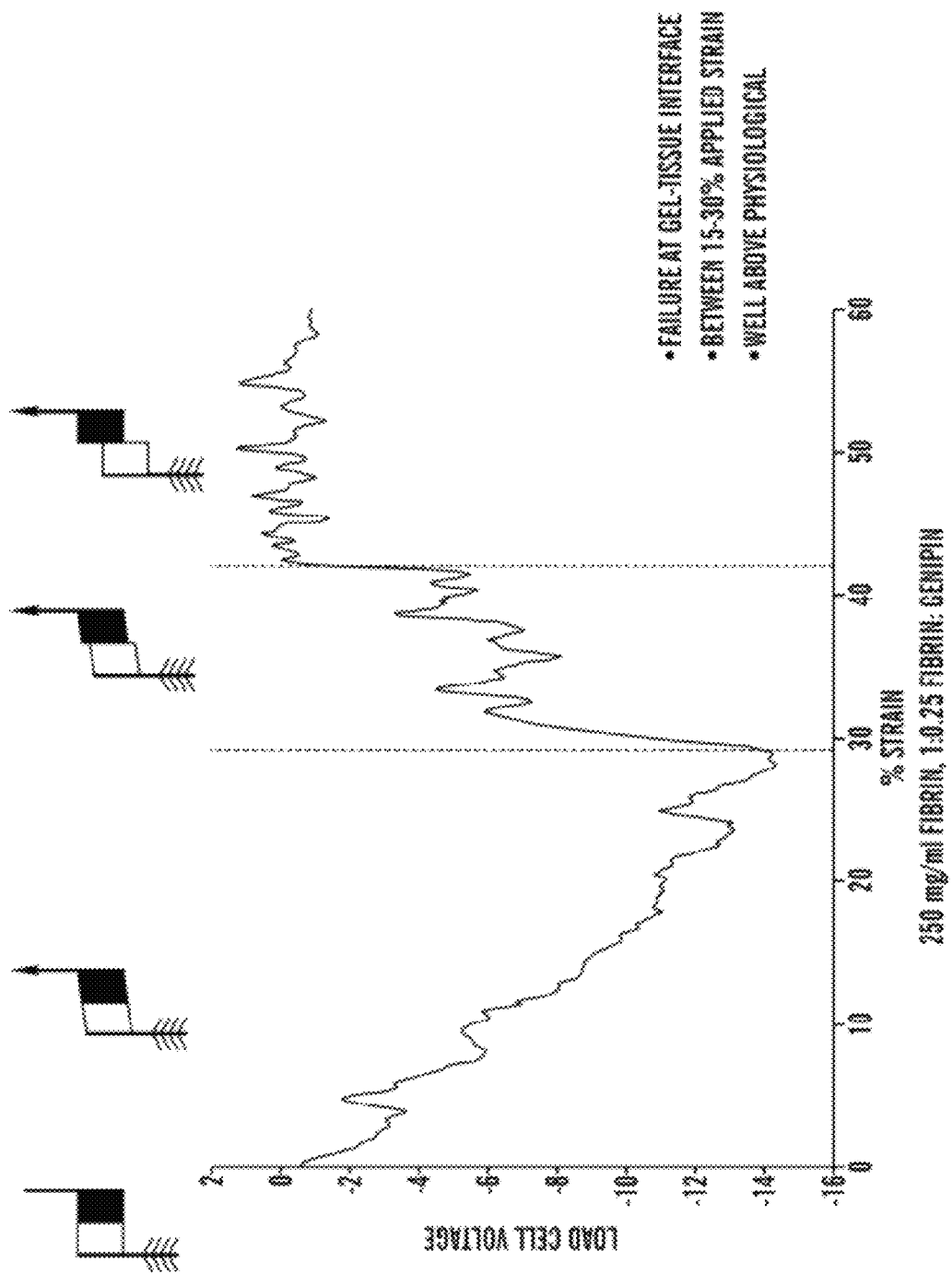
FIG. 9 shows the interface strength of a 1:0.25 fibrin:genipin gel prepared from a 250 mg/ml fibrin solution.
Figure 10:
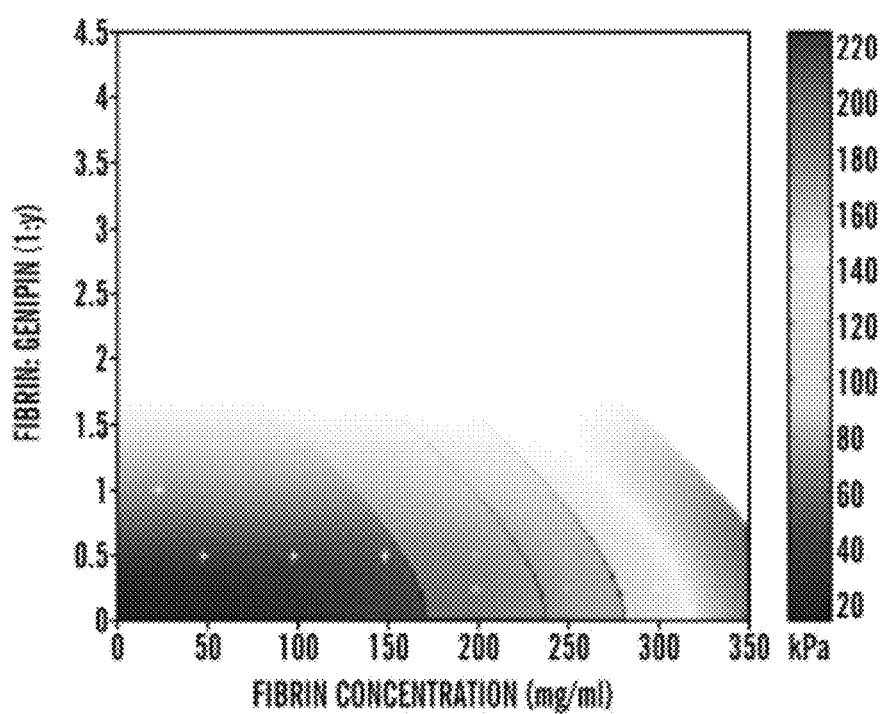
FIG. 10 is a contour graph showing modulus strength of a gel prepared from different concentrations of fibrin solution at different fibrin:genipin ratios.
Figure 11:
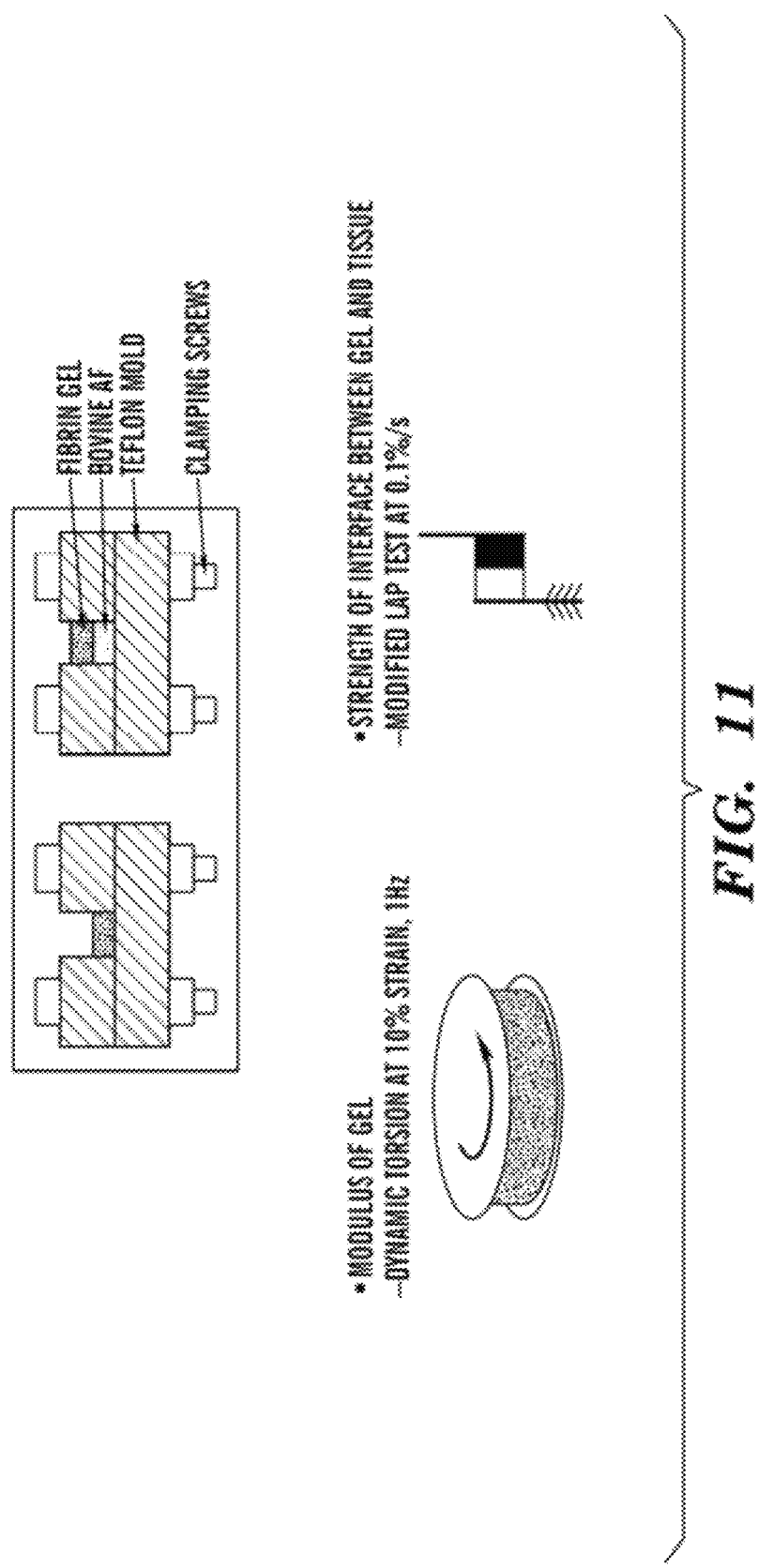
FIG. 11 is a schematic showing the mechanical testing method used in this study.

The cell number was quantified and averaged across 15 fields of view for each condition. Graphs of the cell number over time show similar results for gels with fibrin concentrations of 200 or 250 mg/ml (FIG. 6). Specifically, cells divided rapidly on the gels which contained no genipin. On the cross-linked gels, we observed the cell number to be similar between days 1 and 3; however, multiplication between days 3 and 7 was more rapid and similar in speed to cells on the gels containing no genipin. For both 200 and 250 mg/ml gels, higher cells numbers were seen for genipin:fibrin ratios of 0.25:1 than for 0.5:1. Cell cultured on 300 mg/ml gels multiplied more slowly that those grown on 200 or 250 mg/ml, even in the absence of genipin.

Discussion

An annular repair material should meet three specifications: have a modulus that matches the native annulus tissue, support the growth of disc cells, and maintain adhesion to tissue under physiological strain levels. Accordingly, the invention provides a genipin cross-linked fibrin gel that can meet these requirements. Mechanical results reported herein demonstrate that genipin cross-linked fibrin gels can be created with modulus in an appropriate range. The results reported herein also demonstrated that genipin was required to achieve modulus matching that of native AF tissue across a wide range of strain rates and amplitudes. By altering fibrin concentration and genipin:fibrin ratio, the modulus of the gel was tuneable to specific applications. The results further demonstrate that the ginpin cross-linked fibrin gels descriebd herein were compatible with the in vitro growth of human disc cells. Lastly, the results of lap tests demonstrated that genipin cross-linked fibrin gels remained adhered to pieces of annular tissue at physiological strains of 5-10% (Costi et al., 2007; Krismer et al., 1996; O'Connell et al., 2010) and failed at higher strains of 15-30%.

The gels described herein employ fibrin in conjunction with a genipin crosslinker. The components of fibrin, fibrinogen and thrombin, can be purified from human plasma and fibrin glue has a long history of clinical use in FDA approved products such as Tisseel®, Evicel™, and Crosseal™. Additionally, fibrin has shown to be an excellent scaffold for cell delivery and tissue ingrowth in a number of tissue engineering applications (for review, see Ahmed et al.) (Ahmed et al., 2008). Of specific relevance to connective tissues such as the AF, fibrin has been used to engineer muscle (Hecker et al., 2005; Huang et al., 2005; Nieponice et al., 2007; Rowe et al., 2007), skin (Balestrini and Billiar, 2006; Hojo et al., 2003), cartilage (Connelly et al., 2004; Eyrich et al., 2007; Johnson et al., 2004; Mesa et al., 2006; Passaretti et al., 2001; Peretti et al., 2006), and connective tissue (Chong et al., 2007; Hankemeier et al., 2007). Genipin is a plant-derived crosslinking agent traditionally used in herbal medicine and as a food dye. Genipin has anti-inflammatory activity (Koo et al., 2006) and shows low cytotoxicity as compared to more traditional crosslinkers, such as glutaraldehyde (Bedran-Russo et al., 2007; Tsai et al., 2000). Genipin has previously been used to crosslink a variety of materials including collagenous tissues (Huang et al., 1998; Sung et al., 2003), chitosan (Mi et al., 2002; Mwale et al., 2005), gelatin (Chen et al., 2005), and fibrinogen electrospun scaffolds (Sell et al., 2008).

Genipin crosslinks proteins (including fibrin) by binding amine groups on adjacent proteins; thus degree of crosslinking is dependent on the percentage of amine groups that are bound to a genipin molecule (Touyama et al., 1994; Yao et al., 2004). Unlike absolute genipin concentration, the ratio of genipin:fibrin gives a relative measure of the extent of fibrin crosslinking. Additionally, the cell culture testing showed that rates of cell survival in gels is depended upon genipin: fibrin ratios rather than absolute genipin concentration. For instance, a similar number of cells survived in the 200 mg fibrin/ml gel with a genipin:fibrin ratio of 0.25:1 as in the 300 mg fibrin/ml with a ratio of 0.25:1 gels. This was despite the fact that the absolute genipin concentration was 1.5 times greater in the latter gel. Without wishing to be bound by a theory, cell toxicity largely results from genipin which remains unbound to fibrin. Accordingly, gels with higher ratios of genipin:fibrin had larger amounts of free genipin and resulted in fewer numbers of viable cells in these constructs. Overall, this demonstrates that the ratio of genipin:fibrin is a more relevant variable than absolute genipin concentration.

The results of rheological testing demonstrated power law relationships for the genipin fibrin cross-linked gel as well as human AF tissue. The similarities of material constants of the gel (of certain formulations) with human AF tissue demonstrated strong mechanical compabilility over a large range of frequencies and strain amplitudes. The shear modulus of the gel depends on both the fibrin concentration and the ratio of genipin:fibrin. Increasing the fibrin concentration led to an apparently linear increase in the modulus of the gels. Increasing the ratio of fibrin to genipin, however, did not led to such a regular increase in modulus. Specifically, for a given fibrin concentration, modulus increased steeply from 0:1 to 0.25:1 genipin:fibrin; further increases in modulus were seen only when this ratio was substantially increased to 4:1 (data not shown because cells did not remain viable at this high genipin:fibrin ratio). Without wishing to be bound by a theory, with lower genipin ratios one can maintain mechanical properties while improving cell survival. Furthermore, adjustments in fibrin concentration and/or the ratio of genipin:fibrin allows multiple formulation options to create a gel with the desired modulus.

The Genipin cross-linked fibrin gels described herein meet the basic design requirements for acute annular repair as outlined above. The biomechanical compatibility, "tunable" material properties, and strong adherence to native tissues demonstrate high utility of this biomaterial for AF repair as well as potential repair of other tissues. The "tunable" nature of the mechanical properties demonstrates that one can maintain a desired modulus by simultaneously adjusting the fibrinogen content and the ratio of genipin to fibrin so that one can optimize the formulation for of AF repair or potentially for other tissues with similar design requirements.

The gel's formulation can be altered by augmenting the gel with other compounds and molecules. For example, the gel can be augmented to improve its performance with enzymes to slow degradation. The relatively rapid set time of the gels also enables refinement of delivery and application techniques. Accordingly, the genipin cross-linked fibrin gel described herein can be used as a sealant to repair punctures with injection techniques. The strong adherence of genipin cross-linked fibrin gel to human AF tissues further demonstrates the gel can be used for larger AF defects either alone or in combination with recently developed fibrous materials, creating a composite scaffold with excellent stiffness and adhesive properties (Chang et al., 2007; Mizuno et al., 2004; Nerurkar et al., 2009; Wan et al., 2007).

Accordingly, the invention provides genipin cross-linked fibrin gels that are effective gap filling biocompatible materials with tunable material properties and strong adhesion to native tissues.

REFERENCES

1. Ahmed T A, Dare E V, Hincke M (2008) Fibrin: A Versatile Scaffold for Tissue Engineering Applications. Tissue Eng Part B Rev.

2. Alini M, Roughley P J, Antoniou J, Stoll T, Aebi M (2002) A Biological Approach to Treating Disc Degeneration: Not for Today, but Maybe for Tomorrow. Eur Spine J 11 Suppl 2:S215-220.
3. Balestrini J L, Billiar K L (2006) Equibiaxial Cyclic Stretch Stimulates Fibroblasts to Rapidly Remodel Fibrin. J Biomech 39:2983-2990.
4. Bedran-Russo A K, Pereira P N, Duarte W R, Drummond J L, Yamauchi M (2007) Application of Crosslinkers to Dentin Collagen Enhances the Ultimate Tensile Strength. J Biomed Mater Res B Appl Biomater 80:268-272.
5. Bron J L, Helder M N, Meisel H J, Van Royen B J, Smit T H (2009a) Repair, Regenerative and Supportive Therapies of the Annulus Fibrosus: Achievements and Challenges. Eur Spine J 18:301-313.
6. Bron J L, Koenderink G H, Everts V, Smit T H (2009b) Rheological Characterization of the Nucleus Pulposus and Dense Collagen Scaffolds Intended for Functional Replacement. J Orthop Res 27:620-626.
7. Chang G, Kim H J, Kaplan D, Vunjak-Novakovic G, Kandel R A (2007) Porous Silk Scaffolds Can Be Used for Tissue Engineering Annulus Fibrosus. Eur Spine J 16:1848-1857.
8. Chen Y S, Chang J Y, Cheng C Y, Tsai F J, Yao C H, Liu B S (2005) An in Vivo Evaluation of a Biodegradable Genipin-Cross-Linked Gelatin Peripheral Nerve Guide Conduit Material. Biomaterials 26:3911-3918.
9. Chong A K, Ang A D, Goh J C, Hui J H, Lim A Y, Lee E H, Lim B H (2007) Bone Marrow-Derived Mesenchymal Stem Cells Influence Early Tendon-Healing in a Rabbit Achilles Tendon Model. J Bone Joint Surg Am 89:74-81.
10. Connelly J T, Vanderploeg E J, Levenston M E (2004) The Influence of Cyclic Tension Amplitude on Chondrocyte Matrix Synthesis: Experimental and Finite Element Analyses. Biorheology 41:377-387.
11. Costi J J, Stokes I A, Gardner-Morse M, Laible J P, Scoffone H M, Iatridis J C (2007) Direct Measurement of Intervertebral Disc Maximum Shear Strain in Six Degrees of Freedom: Motions That Place Disc Tissue at Risk of Injury. J Biomech 40:2457-2466.
12. Dare E V, Griffith M, Poitras P, Kaupp J A, Waldman S D, Carlsson D J, Dervin G, Mayoux C, Hincke M T (2009) Genipin Cross-Linked Fibrin Gels for in Vitro Human Articular Cartilage Tissue-Engineered Regeneration. Cells Tissues Organs 190:313-325.
13. Deyo R A, Mirza S K, Martin B I (2006) Back Pain Prevalence and Visit Rates: Estimates from U.S. National Surveys, 2002. Spine (Phila Pa. 1976) 31:2724-2727.
14. Di Martino A, Vaccaro A R, Lee J Y, Denaro V, Lim M R (2005) Nucleus Pulposus Replacement: Basic Science and Indications for Clinical Use. Spine (Phila Pa. 1976) 30:S16-22.
15. Eyrich D, Brandl F, Appel B, Wiese H, Maier G, Wenzel M, Staudenmaier R, Goepferich A, Blunk T (2007) Long-Term Stable Fibrin Gels for Cartilage Engineering. Biomaterials 28:55-65.
16. Hankemeier S, van Griensven M, Ezechieli M, Barkhausen T, Austin M, Jagodzinski M, Meller R, Bosch U, Krettek C, Zeichen J (2007) Tissue Engineering of Tendons and Ligaments by Human Bone Marrow Stromal Cells in a Liquid Fibrin Matrix in Immunodeficient Rats: Results of a Histologic Study. Arch Orthop Trauma Surg 127:815-821.
17. Hecker L, Baar K, Dennis R G, Bitar K N (2005) Development of a Three-Dimensional Physiological Model of the Internal Anal Sphincter Bioengineered in Vitro from Isolated Smooth Muscle Cells. Am J Physiol Gastrointest Liver Physiol 289:G188-196.
18. Hegewald A A, Ringe J, Sittinger M, Thome C (2008) Regenerative Treatment Strategies in Spinal Surgery. Front Biosci 13:1507-1525.
19. Helen W, Gough J E (2008) Cell Viability, Proliferation and Extracellular Matrix Production of Human Annulus Fibrosus Cells Cultured within Pdlla/Bioglass Composite Foam Scaffolds in Vitro. Acta Biomater 4:230-243.
20. Hojo M, Inokuchi S, Kidokoro M, Fukuyama N, Tanaka E, Tsuji C, Miyasaka M, Tanino R, Nakazawa H (2003) Induction of Vascular Endothelial Growth Factor by Fibrin as a Dermal Substrate for Cultured Skin Substitute. Plast Reconstr Surg 111:1638-1645.
21. Huang L L, Sung H W, Tsai C C, Huang D M (1998) Biocompatibility Study of a Biological Tissue Fixed with a Naturally Occurring Crosslinking Reagent. J Biomed Mater Res 42:568-576.
22. Huang Y C, Dennis R G, Larkin L, Baar K (2005) Rapid Formation of Functional Muscle in Vitro Using Fibrin Gels. J Appl Physiol 98:706-713.
23. Johnson T S, Xu J W, Zaporojan V V, Mesa J M, Weinand C, Randolph M A, Bonassar L J, Winograd J M, Yaremchuk M J (2004) Integrative Repair of Cartilage with Articular and Nonarticular Chondrocytes. Tissue Eng 10:1308-1315.
24. Koo H J, Lim K H, Jung H J, Park E H (2006) Anti-Inflammatory Evaluation of Gardenia Extract, Geniposide and Genipin. J Ethnopharmacol 103:496-500.
25. Krismer M, Haid C, Rabl W (1996) The Contribution of Anulus Fibers to Torque Resistance. Spine (Phila Pa. 1976) 21:2551-2557.
26. Lavik E, Langer R (2004) Tissue Engineering: Current State and Perspectives. Appl Microbiol Biotechnol 65:1-8.
27. Lee C K (1988) Accelerated Degeneration of the Segment Adjacent to a Lumbar Fusion. Spine (Phila Pa. 1976) 13:375-377.
28. Mesa J M, Zaporojan V, Weinand C, Johnson T S, Bonassar L, Randolph M A, Yaremchuk M J, Butler P E (2006) Tissue Engineering Cartilage with Aged Articular Chondrocytes in Vivo. Plast Reconstr Surg 118:41-49; discussion 50-43.
29. Mi F L, Tan Y C, Liang H F, Sung H W (2002) In Vivo Biocompatibility and Degradability of a Novel Injectable-Chitosan-Based Implant. Biomaterials 23:181-191.
30. Mizuno H, Roy A K, Vacanti C A, Kojima K, Ueda M, Bonassar L J (2004) Tissue-Engineered Composites of Anulus Fibrosus and Nucleus Pulposus for Intervertebral Disc Replacement. Spine (Phila Pa. 1976) 29:1290-1297; discussion 1297-1298.
31. Mwale F, Iordanova M, Demers C N, Steffen T, Roughley P, Antoniou J (2005) Biological Evaluation of Chitosan Salts Cross-Linked to Genipin as a Cell Scaffold for Disk Tissue Engineering. Tissue Eng 11:130-140.
32. Nerurkar N L, Baker B M, Sen S, Wible E E, Elliott D M, Mauck R L (2009) Nanofibrous Biologic Laminates Replicate the Form and Function of the Annulus Fibrosus. Nat Mater 8:986-992.
33. Nerurkar N L, Elliott D M, Mauck R L (2007) Mechanics of Oriented Electrospun Nanofibrous Scaffolds for Annulus Fibrosus Tissue Engineering. J Orthop Res 25:1018-1028.
34. Nieponice A, Maul T M, Cumer J M, Soletti L, Vorp D A (2007) Mechanical Stimulation Induces Morphological and Phenotypic Changes in Bone Marrow-Derived Progenitor Cells within a Three-Dimensional Fibrin Matrix. J Biomed Mater Res A 81:523-530.

35. O'Connell G D, Vresilovic E J, Elliott D M (2010) Human Intervertebral Disc Internal Strain in Compression: The Effect of Disc Region, Loading Position, and Degeneration. J Orthop Res.
36. Passaretti D, Silverman R P, Huang W, Kirchhoff C H, Ashiku S, Randolph M A, Yaremchuk M J (2001) Cultured Chondrocytes Produce Injectable Tissue-Engineered Cartilage in Gel Polymer. Tissue Eng 7:805-815.
37. Peretti G M, Xu J W, Bonassar L J, Kirchhoff C H, Yaremchuk M J, Randolph M A (2006) Review of Injectable Cartilage Engineering Using Fibrin Gel in Mice and Swine Models. Tissue Eng 12:1151-1168.
38. Rowe S L, Lee S, Stegemann J P (2007) Influence of Thrombin Concentration on the Mechanical and Morphological Properties of Cell-Seeded Fibrin Gels. Acta Biomater 3:59-67.
39. Sato M, Asazuma T, Ishihara M, Kikuchi T, Masuoka K, Ichimura S, Kikuchi M, Kurita A, Fujikawa K (2003) An Atelocollagen Honeycomb-Shaped Scaffold with a Membrane Seal (Achms-Scaffold) for the Culture of Annulus Fibrosus Cells from an Intervertebral Disc. J Biomed Mater Res A 64:248-256.
40. Schlegel J D, Smith J A, Schleusener R L (1996) Lumbar Motion Segment Pathology Adjacent to Thoracolumbar, Lumbar, and Lumbosacral Fusions. Spine (Phila Pa. 1976) 21:970-981.
41. Sebastine I M, Williams D J (2007) Current Developments in Tissue Engineering of Nucleus Pulposus for the Treatment of Intervertebral Disc Degeneration. Conf Proc IEEE Eng Med Biol Soc 2007:6401-6406.
42. Sell S A, Francis M P, Garg K, McClure M J, Simpson D G, Bowlin G L (2008) Cross-Linking Methods of Electrospun Fibrinogen Scaffolds for Tissue Engineering Applications. Biomed Mater 3:45001.
43. Shao X, Hunter C J (2007) Developing an Alginate/Chitosan Hybrid Fiber Scaffold for Annulus Fibrosus Cells. J Biomed Mater Res A 82:701-710.
44. Sung H W, Chang W H, Ma C Y, Lee M H (2003) Crosslinking of Biological Tissues Using Genipin and/or Carbodiimide. J Biomed Mater Res A 64:427-438.
45. Touyama R, Inoue K, Takeda Y, Yatsuzuka M, Ikumoto T, Moritome N, Shingu T, Yokoi T, Intuye H (1994) Studies on the Blue Pigments Produced from Genipin and Methylamine Ii: The Formation Mechanisms of Brownish-Red Intermediates Leading to the Blue Pigment Formation. Chem Pham Bull 42:1571-1578.
46. Tsai C C, Huang R N, Sung H W, Liang H C (2000) In Vitro Evaluation of the Genotoxicity of a Naturally Occurring Crosslinking Agent (Genipin) for Biologic Tissue Fixation. J Biomed Mater Res 52:58-65.
47. Wan Y, Feng G, Shen F H, Balian G, Laurencin C T, Li X (2007) Novel Biodegradable Poly(1,8-Octanediol Malate) for Annulus Fibrosus Regeneration. Macromol Biosci 7:1217-1224.
48. Wan Y, Feng G, Shen F H, Laurencin C T, Li X (2008) Biphasic Scaffold for Annulus Fibrosus Tissue Regeneration. Biomaterials 29:643-652.
49. Wilke H J, Heuer F, Neidlinger-Wilke C, Claes L (2006) Is a Collagen Scaffold for a Tissue Engineered Nucleus Replacement Capable of Restoring Disc Height and Stability in an Animal Model? Eur Spine J 15 Suppl 3:S433-438.
50. Yao C H, Liu B S, Chang C J, Hsu S H, Chen Y S (2004) Preparation of Networkds of Gelatin and Genipin as Degradable Biomaterials. Mater Chem and Phys 83:204-208.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A genipin cross-linked fibrin gel for repairing defects in a intervertebral disc annulus, the gel having a genipin:fibrin ratio of 0.1:1 to 2:1, where the gel is made with a fibrin solution comprising from 250 mg/ml to 400 mg/ml of fibrin.
2. The gel of claim 1, wherein gel has a shear modulus of from about 50 kPa to about 110 kPa.
3. The gel of claim 1, wherein the gel further comprises a bioactive agent.
4. The gel of claim 3, wherein the bioactive agent is a therapeutic agent.
5. The gel of claim 3, wherein the bioactive agent is a wound healing agent.
6. The gel of claim 1, wherein the gel further comprises a cell.
7. The gel of claim 6, wherein the cell is mammalian cell.
8. The gel of claim 6, wherein the cell is a human cell.
9. The gel of claim 6, wherein the cell is a disc cell.
10. The gel of claim 1, wherein the gel is functionalized with an affinity binding molecule, wherein the affinity molecule binds with a bioactive molecule.
11. The gel of claim 10, wherein the affinity molecule is selected from the group consisting of antibodies, antigens; lectins; proteins; peptides; nucleic acids; receptor molecules; and ligands for receptors.
12. The gel of claim 10, wherein the affinity molecule binds with a cell.
13. A method of repairing a tissue defect in an intervertebral disc annulus in a subject in need thereof, the method comprising placing a gel of claim 1 at a tissue defect site in the subject.
14. The method of claim 13, wherein the tissue defect is selected from the group consisting of wounds, ulcers, burns, natural defects, and any combinations thereof.
15. The method of claim 13, wherein the tissue defect is caused by traumatic injury, disease, infection, surgical intervention, natural causes, or any combinations thereof.
16. The method of claim 13, wherein the tissue defect is an intervertebral disc annulus defect.
17. The method of claim 13, wherein the subject is a mammal.
18. The method of claim 13, wherein the subject is human.

* * * * *